United States Patent [19]

Buchheit

[11] Patent Number: 4,910,193
[45] Date of Patent: Mar. 20, 1990

[54] TREATMENT OF GASTROINTESTINAL DISORDERS

[75] Inventor: Karl-Heinz Buchheit, Lörrach

[73] Assignee: Sandoz Ltd., Basel, Switzerland

[21] Appl. No.: 90,986

[22] Filed: Aug. 28, 1987

Related U.S. Application Data

[63] Continuation of Ser. No. 809,541, Dec. 16, 1985, abandoned.

[51] Int. Cl.$^4$ .................... A61K 31/34; A61K 31/38; A61K 31/405; A61K 31/435
[52] U.S. Cl. ................................ 514/216; 514/183; 514/210; 514/212; 514/277; 514/294; 514/295; 514/296; 514/299; 514/305; 514/319; 514/320; 514/323; 514/324; 514/408; 514/413; 514/414; 514/415; 514/428
[58] Field of Search .............. 548/512, 452, 454, 455, 548/460; 546/137, 196, 201, 202, 205, 206, 112; 540/477, 582; 514/212, 277, 305, 408, 428, 414, 210, 183, 216, 299

[56] References Cited

U.S. PATENT DOCUMENTS

| | | | |
|---|---|---|---|
| 2,857,383 | 10/1958 | Voegtli | 546/202 |
| 3,838,169 | 9/1974 | Thominet | 546/202 |
| 4,141,884 | 2/1979 | Irick, Jr. et al. | 546/196 |
| 4,182,703 | 1/1980 | Irick, Jr. et al. | 546/202 |
| 4,721,720 | 1/1988 | Wootton et al. | 546/202 |
| 4,725,603 | 2/1988 | Sanger et al. | 546/202 |

FOREIGN PATENT DOCUMENTS

| | | | |
|---|---|---|---|
| 897117 | 12/1983 | Belgium | 546/202 |
| 0900425 | 2/1985 | Belgium | 546/202 |
| 0901274 | 6/1985 | Belgium | 546/202 |
| 0013138 | 12/1979 | European Pat. Off. | 546/196 |
| 0201165 | 3/1986 | European Pat. Off. | 546/196 |
| 1932933 | 1/1970 | Fed. Rep. of Germany | 546/196 |
| 8403281 | 2/1983 | PCT Int'l Appl. | 546/196 |
| 1233268 | 5/1971 | United Kingdom | 546/137 |

OTHER PUBLICATIONS

Chem. Abstracts; vol. 100; No. 209629q.
Meeting of British Pharm. Society, Abstract No. 52, Apr. (1986).

*Primary Examiner*—Mary C. Lee
*Assistant Examiner*—J. Richter
*Attorney, Agent, or Firm*—Gerald D. Sharkin; Robert S. Honor; Joseph J. Borovian

[57] ABSTRACT

Use of a mono or dicyclic carboxylic or heterocyclic carboxylic acid ester or amide of an alcohol or amine nitrogen as a ring atom in free base form or in acid addition or quaternary ammonium salt form as a 5-HT$_3$ antagonist in the manufacture of a medicament suitable for the treatment of serotonin induced gastrointestinal disturbances.

16 Claims, No Drawings
}

TREATMENT OF GASTROINTESTINAL DISORDERS

This is a continuation of application Ser. No. 809,541, filed Dec. 16, 1985 now abandoned.

The invention relates to the treatment of gastrointestinal disorders, especially with mono- or dicyclic carboxylic acid or heterocyclic carboxylic acid esters and amides of cyclic alcohol or amine containing nitrogen as a ring atom. These compounds are referred to hereinafter as compounds of the invention.

Belgian Patent Nos. 897,117, 900,425 and 901,274 disclose classes of such acids and amides which are stated to have serotonin M antagonistic activity (also known as 5-$HT_3$ antagonism).

The contents of these patents are incoporated herein by reference. The compounds disclosed have the following formula I:

A-B-C-D      I wherein
A is a group of formula

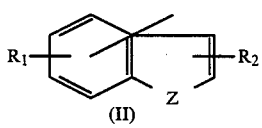
(II)

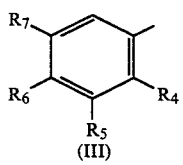
(III)

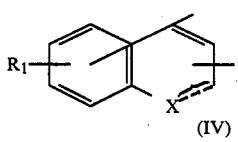
(IV)

or

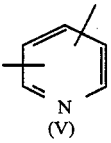
(V)

wherein
the free valence is attached to either fused ring in formula (II) or (IV),
X-Y is —CH=CH—, —O—CH$_2$— or —N=CH—,
Z is —CH$_2$—, —NR$_3$—, —O— or —S—,
$R_1$ and $R_2$ are independently hydrogen, halogen, ($C_{1-4}$)alkyl, ($C_{1-4}$)alkoxy, hydroxy, amino, ($C_{1-4}$)alkylamino, di($C_{1-4}$)alkylamino, mercapto or ($C_{1-4}$)alkylthio,
$R_3$ is hydrogen, ($C_{1-4}$)alkyl, ($C_{3-5}$)alkenyl, aryl or arylalkyl, and
$R_4$ to $R_7$ are, independently, hydrogen, amino, nitro, ($C_{1-4}$)alkylamino, di($C_{1-4}$)alkylamino, halogen, ($C_{1-4}$)alkoxy, ($C_{1-4}$)alkyl, ($C_{1-4}$)alkanoylamino, pyrrolyl, sulfamoyl or carbamoyl,
B is —CO— or —SO$_2$—,
C is —O— or —NH—, and
D is a group of formula

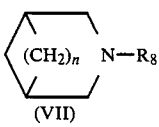
(VI)

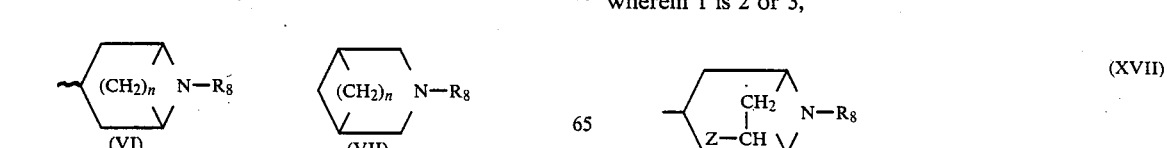
(VII)

wherein n is 2, 3 or 4

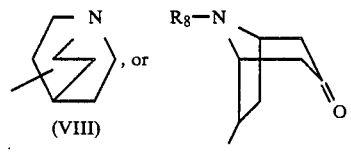
(VIII)    (IX)

wherein $R_8$ is hydrogen, ($C_{1-7}$)alkyl, $C_{(3-5)}$alkenyl or aralkyl, and,
when B is CO, additionally D may be a group of formula

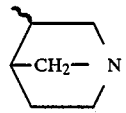
(X)

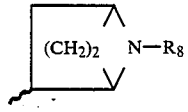
(XI)

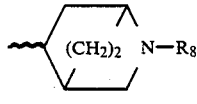
(XII)

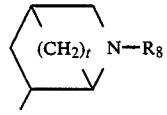
(XIII)

wherein t is 1 or 2, and $R_8$ is as defined above,

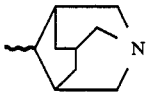
(XIV)

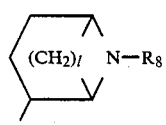
(XV)

wherein the bond is in the position 3 (*) or 4 [*],

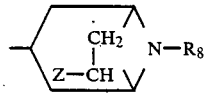
(XVI)

wherein 1 is 2 or 3, (XVII)

wherein Z is ($C_{1-4}$)alkoxy,

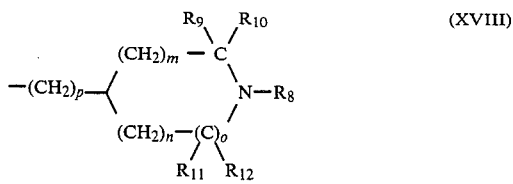

wherein $R_9$ to $R_{12}$ are independently hydrogen or $(C_{1-4})$alkyl, m is 0, 1 or 2 and n, o, p independently are 0 or 1, with the proviso that, when A is formula III, B is CO and C is NH, D is not a group of formula VI.

The essentially antagonistic action against 5-HT of the preferred compound ICS 205-930, indol-3-yl carboxylic acid endo-8-methyl-8-aza-bicyclo-[3,2,1]oct-3-yl ester on the rabbit vagus, rabbit heart and guinea pig ileum has been described (P. Donatsch et al., Br. J. Pharmacol. 1984, 81, 348), and also its topical application to humans as the first 5-HT$_3$ antagonist. It was stated to be a competitive antagonist of the 5-HT$_3$ receptors in the guinea pig ileum on the basis of the effect of the compound in counteracting 5-HT induced spasms, these spasms being prolonged and permanent contractions. Moreover, no analysis was disclosed of its action in the guinea pig ileum.

Several drugs e.g. metoclopramide are known for the treatment of gastrointestinal disorders (gut motility disorders). Action has been ascribed to opiates (e.g. loperamide), dopaminergic compounds (e.g. metoclopramide) although for most drugs the mode of the action is not well understood (see J. R. Malegeleda Scand. J. Gastroenterology, 19, Suppl. 96, 1984, pp. 115–121). Thus metoclopramide has been shown to have an IC$_{50}$ of about 170 nM/liter in binding studies with dopamine sites with tritiated haloperidol.

European Patent Publication 13138 discloses benzoic acid amides of piperidylamines having an alkylene bridge across ring positions 2 and 6. The compounds are stated to be active inter alia in increasing the intragastric pressure in the rat, in reversing the apomorphine induced delay in gastric emptying in the rat, and inhibiting the apomorphine-induced emetic effect in the rat. The compounds are indicated to be dopamine antagonists and useful in the treatment of impaired gastrointestinal motility, such as retarded gastric emptying, dyspepsia, flatulence, esophageal reflux, peptic ulcer and emesis.

The compounds of the present invention in general do not significantly affect apomorphine-induced symptoms. They show on the other hand a long lasting and potent effect in the treatment of serotonin-induced gastrointestinal disturbances by action on 5-HT$_3$ receptors. The compounds of the invention have thus a different mechanism of action to that stated for those in European Patent Publication 13138 and are well tolerated.

Peristaltic movements (Peristaltis) are coordinated contractions and are necessary for the proper functioning of the gastrointestinal system. We have now found that activation of 5-HT$_3$ receptors are involved in provocation of abnormal peristaltic movements and associated gastrointestinal disorders of motility and secretion. Also we have found that serotonin antagonists are useful in decreasing increased peristaltic movements in the intestines and increasing decreased peristaltic movements in the stomach, and are hence useful in the treatment of disorders of gastric motility.

We have found that reflexes responsible for different kinds of intestinal reactions such as smooth muscle contractions, secretion by mucosal cells and/or dilation of intestinal blood vessels, a pre-requisite for the secretion of fluids are stimulated by stimulation of 5-HT$_3$ receptors located on afferent sensory neurons by 5-HT$_3$ released on the serosal side and are blocked by 5-HT$_3$ antagonists.

In formula I the preferences are as in the above Belgian Patents, e.g. aryl is preferably phenyl, arylalkyl is conveniently benzyl.

One group of compounds of formula I comprises compounds wherein A is formula II or III, wherein $R^4$ to $R^7$ are other than sulfamoyl or carbamoyl, D is VI or VIII with the proviso when A is III and C is —NH—, D is VIII.

Preferred compounds of the invention include:

Indol-3-yl carboxylic acid endo-8-methyl-8-aza-bicyclo-[3,2,1]oct-3-yl ester [hereinafter compound E].

Benzo[b]thiophen-3-yl carboxylic acid endo-9-methyl-aza-bicyclo[3,3,1]non-3-yl ester [hereinafter compound F].

5-fluoro-1-methyl-indol-3-yl carboxylic acid endo-9-methyl-9-aza-bicyclo[3,3,1]non-3-yl ester [hereinafter compound G and also the compound of example 41].

The action of the compounds of the invention is shown in the following tests:

TEST A

The compounds of the invention facilitate field stimulation-induced contractions in muscle strips from different parts of the guinea pig stomach and are therefore indicated to increase decreased peristalic movements in the stomach and to enhance gastric emptying in vivo. The test is effected as follows:

Male Dunkin-Hartley guinea pigs, 340–450 g, which had been starved overnight, were killed by cervical transsection and the stomach removed and placed in Krebs-Henseleit solution (NaCl 118.0, KCl 4.75, KH$_2$PO$_4$ 1.2, MgSO$_4$ 1.2, CaCl$_2$ 2.5, glucose 10 mM). Segments were taken from the body (approximately 20 mm long, 3–4 mm wide) with dissection in a plane suitable to investigate tension changes in the circular muscle layer. Tissues were placed in 30 ml organ baths containing oxygenated (95% O$_2$, 5% CO$_2$) Krebs-Henseleit solution at 37° C. One gram tension was applied to the tissues which were allowed to equilibrate for 45–60 min. before electrical stimulation. Intramural stimulation was achieved by using platinum wire electrodes placed approximately 5 mm apart, current being obtained from a Farnell Physiological stimulator. Tension changes were detected by Grass tension transducers and displayed on a multichannel Grass recorder. A frequency-response curve was initially constructed in the absence of test substance and then in the presence of the test substance which was allowed a 45 min. pretreatment time. The second curve was related to the first to assess the degree of potentiation or antagonism. Tissues were stimulated for 30 s at 5 min. intervals. Fresh tissues were used to assess such antagonist interaction. Appropriate solvent control experiments were carried out throughout the studies. Responses were measured as changes in gram tension, but to allow easier comparison between treatments, data was converted to show changes as percentage values. The significance of differences between control responses and those obtained in the presence of interacting drugs was assessed using the Mann-Whitney U test.

The compounds of the invention are active at about $10^{-7}$M to about $10^{-9}$ Molar and induce frequency related increases in contraction responses.

Compound E produced a maximal response at $10^{-8}$M was 100 times more active then metoclopromide.

TEST B

The compounds of the invention also induce gastric emptying as indicated in standard in vivo tests, e.g. in conscious guinea pigs having stomachs made atonic (i.e. having decreased peristaltic movements) by fasting and wherein the passage of glass spheroids was observed by X-ray techniques. The experiments is effected as follows:

Food was withdrawn for 14 hours before the measurement of gastric emptying. The experiment was conducted under low illumination with minimal noise and disturbance, and was carried out only by those experimentors who had daily contact with the guinea pigs and who carried out the initial training to accustom the guinea pigs to handling. Therefore, animals were subject to minimal stress. Measurement of gastric emptying was achieved by X-ray location (50 KV, 30 mA, 0.5–0.9 s) using Kodak plates (NS-2T, 13×18 cm) of polystyrene-coated barium sulphate spheroids (approximately 30, 1 mm in diameter) which were swallowed by the guinea pigs when placed in the back of the mouth in 0.2 ml of 1% carboxymethycellulose with 0.05 ml glycerin to initiate prompt and voluntary swallowing. The passage of the spheroids was followed for 3–4 h: during this period animals were placed in their normal housing cages and were only removed 5 min to prior to X-ray (at 30–60 min. intervals) when they were placed in an individual perspex holding case which held the animal comfortably in a stable position: the holding case was correctly shaped (33×15 cm, and 13 cm high) to hold a 450–550 g guinea pig between foam-lined sides and an animal trained to entering the cage would do so and remain quiet and unstressed during the X-ray procedure. Gastric emptying was measured as the number of spheroids leaving the stomach.

Six guinea pigs were used at each dose level of drug and responses compared to those of guinea pigs receiving the appropriate vehicle. The significance of differences between drug and control responses was assessed using the Mann Whitney U test.

The compounds of the invention are active at doses of about 0.01 to about 1 mg/kg i.p. in enhancing gastric emptying. Compound E was about 50 times more active than metoclopramide.

The effect of the compounds increasing gastric emptying indicates a increased tonus on gastrointestinal tract.

The compounds of the invention are also useful in inhibiting increased peristaltic movements in the intestines as indicated in the following tests.

TEST C

In a further test the inhibition of the compounds of the invention in inhibiting the increase in gastrointestinal motility induced by 5-hydroxytryptophan (5-HTP) was observed.

Male NMRI mice (18–32 g in weight) are deprived of food 20 hours before the test. Water is not limited. The animals are separated by a barrier from their straw and access to feces. At the beginning of the test the animals are separated in individual single cages and water is removed.

All animals were treated with the test compound or saline. I.p. administration was used. Injection volume was 0.1 ml/10 g. 30 minutes after pre-treatment 5-HTP or saline was administered. Injection volume 0.1 ml/10 g. Dose 3 mg/kg. At the same time charcoal was administered perorally (10% suspension in water; 0.1 ml/10 g). 45 minutes after the start of the experiment the animals were killed. The intestines from the stomach to the rectum were examined. For each animal the transit distance of the front of the charcoal mean along the intestine was measured. The distance was ascertained as a percentage of the whole intestinal length. Groups of at least 3 animals were used.

The compounds of the invention inhibit 5-HTP induced motility at doses of about 10 to 100 μg/kg i.p.

|  | $ED_{50}$ i.p. |
| --- | --- |
| Compound E | 70 μg/kg |
| Compound F | 25 μg/kg |
| Compound G | 2 μg/kg |

TEST D

In a further test the compounds are shown to inhibit chloera toxin-induced secretory diarrhea which leads to increased perstaltic motility.

Method

Male NMRI mice (20–30 g) were deprived of food for 24 hours, but had free access to water. For the duration of the experiment water was subsequently withdrawn. Saline or the test compound were administered intraperitoneally. Four dose levels of each drug were investigated and each dose was given to 5 animals. One hour after pre-treatment with the drug the animals were challenged with 200 μg of pure cholera toxin p.o. through a tube to the stomach followed by 2 ml of the above Tyrode solution. Three hours later the administration of the test compounds was repeated. Four hours after the cholera toxin challenge the animals were killed and the content of the whole intestine determined by weighing.

Administration protocol 0 hours: Administration of test compound
1 hour: Administration of cholera toxin
3 hours: Repeated addition of test compound
4 hours: Sacrifice of animals.

The intestinal contents are usually increased under the influence of cholera toxin. This effect was reduced by 50% by the test compounds, in particular by 50% at a dose of 100 to 500 micrograms/kg. An increase in the dose of compound E did not lead to a reduction in the stomach contents.

The isolated longitudinal muscle of the guinea pig ileum with its adhering myenteric plexus is a well established model which permits investigation of the mechanism of action of various neurotransmitters. It does not, however, indicate by itself action of the compounds on peristaltic movements.

Method

Male guinea pigs (200–400 g) were killed by a blow on the head and exsanguineated. A length of small intestine was removed about 2 cm from the ileo-caecal valve. The mesentery was carefully removed and the ileum was stretched over a glass rod. By stroking tangentially away from the mesenteric attachement with a wad of cotton wool, the longitudinal muscle layer was separated and stripped from the unterlying circular muscle. Longitudinal muscle strips, 3-4 cm length, were mounted in a 10 ml organ bath containing Tyrode solution at 37° C. and bubbled with 5% carbon dioxide in oxygen. The Tyrode solution was of the following composition (mmol/l): NaCl, 137.0; $CaCl_2$, 1.8; KCl, 2.7; $MgCl_2$, 1.05; $NaHCO_3$, 11.9; $NaH_2PO_4$, 0.4; glucose, 5.6. The strips were placed under a resting tension of 500 mg. Contractions were recorded with an isotonic pendulum lever. After equilibration for 30 min a set concentration of carbachol was applied in 10 min intervals until a consistent reaction was achieved.

Production of the concentration/reaction curve

Non-cumulative concentration-response curves for 5-HT were established by adding increasing concentrations of the agonist to the organ bath at intervals of at least 15 min. Preceding experiments showed that the intervals were long enough to avoid tachyphylaxis. Each concentration was left in contact with the tissue for 1 min. Each strip was only used to record two concentration-response curves; the first for 5-HT alone and the second for 5-HT in the presence of a set concentration of antagonist, each strip thus serving as its own control. Antagonists were allowed to preequilibrate for at least 10 min prior to addition of 5-HT. The contractions expressed as percentage of the maximal response to 5-HT obtained from several preparations were plotted as mean values in order to obtain log-concentration-response curves. Inhibition constants were expressed in the form of $pA_2$ values which were graphically determined according to conventional methods (Arunlakshana and Schild, 1959. McKay 1978).

In this test 5-HT elicits a concentration-dependent contractile effect. 5-HT induces its major contractile effects in the longitudinal muscle strip of the guinea pig ileum by releasing substance P from nerve endings within this tissue. Its effect is mediated by two different 5-HT receptors. At low concentrations 5-HT activates a neuronal receptor which causes substance P release. The liberated substance P activates neuronal substance P receptors and this causes the release of acetylcholine which subsequently activates muscarinic receptors located on smooth muscle cells and brings about contraction. At higher concentrations 5-HT activates a second neuronal receptor which results in release of sufficient quantities of substance P to cause activation of substance P receptors on smooth muscle cells and thereby cause contraction.

The compounds of the invention block preferentially the low affinity 5-HT receptors thereby inhibiting 5-HT-induced contraction e.g. at concentrations from about $10^{-7}$ to about $10^{-9}$ mol/liter.

|  | high affinity receptor | low affinity recept. |
| --- | --- | --- |
| Compound E | $pD'_2 = 5.7$ | $pA_2 = 7.9$ |
| Compound F | $pD'_2 = 5.9$ | $pA_2 = 9.4$ |

In this test the ratio between the $pA_2$ value and the $pD'_2$ value is conveniently greater than 100, more preferably 1000.

The compounds have little affinity for the high affinity 5-HT receptor indicated to be responsible for controlling secretion and motility processes involving acetylcholine release, but have greater affinity for the low affinity serotonin receptor sub-type which is indicated to be involved in pathophysiological abnormal peristaltic movements conditions such as gastroparesis (lack of stomach motility) or diarrhea.

The compounds of the invention preferentially inhibit the 5-HT reflex without affecting the basal reflex activity and to an increase in peristaltic movements. This is in contrast to drugs like atropine which paralyse the whole reflex, and metoclopramide which has dopamine agonist action.

In the charcoal meal test in the rate at doses of over 50 mg/kg s.c. of the compounds of the invention the influence on normal gastric motility is not significant.

The compounds of the invention have insignificant action on dopamine binding sites, e.g. having an $IC_{50}$ of 100 mM/liter or more using tritriated haloperidol. Thus Example 71 hereinafter has an $IC_{50}$ of greater than 10,000 mM/liter.

Gastrointestinal disorders which result from increased peristaltic movements in the intestinal tract or from decreased peristaltic movements in the stomach are therefore indicated to be treated by blockade of 5-$HT_3$ neuronal receptors. The compounds of the invention are indicated for use in the treatment of gastrointestinal disorders. The compounds also inhibit or prevent the action of 5-HT on low affinity 5-HT receptors in the gastrointestinal tract, and therefore are indicated for use in the treatment of gastroparesis or disturbances of motility. They are also indicated for use in gastrointestinal disorders where an abnormal increase in the synthesis or liberation of 5-HT from the enterochromaffin cells or neurons taken places without significantly affecting basal secretion or motility. They are also indicated to be well tolerated.

The compounds of the invention are therefore useful in the treatment of gastrointestinal disturbances which require antagonism of 5-$HT_3$ receptors.

Compounds of formula III are particularly indicated for use in increasing decreased peristaltic movements in the stomach. Preferred compounds are those of Examples 54, 56, 57, 71, 84, 85 and 98 hereinafter. Compounds of formula II are particularly indicated for use in decreasing increased peristaltic movements in the intestines. Preferred compounds are compounds E and F.

The compounds are useful in the treatment of disorders resulting from increased peristaltic movements in the intestines and intestinal disorders arising or from activation of 5-$HT_3$ receptors, including diarrhea, e.g. secretory diarrhea, bacterial induced diarrhea, choleic diarrhea, traveller's diarrhea and psychogenic diarrhea, Crohn's disease, spastic colon and irritable bowel syndrome. The compounds are also indicated to be useful in the treatment of disorders due to hypersecretion in the intestines, e.g. as a result of inflammation such as arising out of gastritis, peptic ulcer, biliary dyskinesia, appendicitis, ulcerative colitis and due to carcinoid syndrome leading to increased 5-HT secretion.

Furthermore, the compounds are useful in the treatment of disorders arising from decreased peristaltic movements in the stomach and/or stomach disorders arising from activation of 5-$HT_3$ receptors, including those arising from decreased gastric emptying, including treatment of oesophageal motility disturbances, achalasia, hiatus hernia, cardia insufficiency, gastroesophageal and gastroduodeinal reflux, stomach hypotonia and pylorus hyperplasia.

Furthermore, the compounds are useful in the treatment of paralytic ileus and Hirschsprung's disease.

In one aspect the present invention proves a use of a mono or dicyclic carboxylic or heterocyclic carboxylic acid ester or amide of a alcohol or amine containing nitrogen as a ring atom in free base form or in acid addition or quaternary ammonium salt form as a 5-HT$_3$ antagonist in the manufacture of a medicament suitable for the treatment of serotonin induced gastrointestinal disturbances. Preferably the compound is a compound of formula I.

For these indications, the exact dosage will, of course, vary depending upon the compound employed, mode of administration and treatment desired. In general, satisfactory results are obtained in doses about 0.01 to about 10 mg/kg. For the larger primates, in particular humans, an indicated daily dosage is in the range from about 0.5 mg to about 500 mg (e.g. 20 to 200, or 20 to 100 mg or 20 to 400 mg), of a compound of formula I conveniently administered, for example, in divided doses 2 to 4 times a day. Unit dosage forms contain, for example, from about 0.1 mg to about 250 mg of the compound. If desired, the compounds may be administered in a single dose for acute therapy.

The compounds E and F are the preferred compounds.

The compounds of the invention may be administered in similar manner to known standards for use in these indications. The suitable daily dosage for a particularly compound will depend on a number of factors, such as its relative potency of activity.

On the basis of the activity of the compound E in the above tests, an indicated daily dose for the compound E is from about 5 to about 20 mg p.o. for larger primates such as humans.

The compounds of formula I may be administered in free base form or in pharmaceutically acceptable acid addition salt form or in a quaternary ammonium salt form. Such salts may be prepared in conventional manner and are in general known. They exhibit the same order of activity as the free base form and pharmaceutical compositions comprise a compound of formula I in free base or pharmaceutically acceptable acid addition salt form or quaternary ammonium salt formm in association with pharmaceutical carrier or diluent. Such compositions may be manufactured in conventional manner.

The specific compounds maintained hereinafter are preferred to be administered in the salt form mentioned in the above mentioned Belgian patents, e.g. Compound E as the hydrochloride. The compounds F and G have previously only been disclosed in the free base form. We have now found that compounds E and G are preferably used e.g. in pharmaceutical compositions in the form of the hydrochloride of compound F (m.pt. 242°–243° C.) and hydrogen maleate of compound G (m.pt. 171°–172° C.). These forms have been found to have especially advantageous properties, e.g. from the solubility and stability point of view.

The compounds may be administered by any conventional route, in particular enterally, preferably orally, e.g. in the form of tablets or capsules or parenterally, e.g. in the form of injectable solutions or suspensions.

Suitable pharmaceutical carriers and diluents for oral administration include polyethylene glycol, polyvinyl-pyrrolidone, mannitol, lactose etc. granulating agents, and disintegrating agents such as starch and algenic acid, binding agents such as stearic and gelatine, lubricating agents such as magnesium stearate. stearic acid and talc. Suspensions may contain conserving agents like ethyl p-hydroxy-benzoate, suspending agents such as methyl-cellulose, tenside etc. For parenteral forms the compositions are preferably buffered, aqueous solutions (pH between 4 and 5).

In one group of compounds the compounds of formula I is a group of formula II, in particular Z is NR$_3$, O, or S.

In another group the compound of formula I has a group of formula III. In a sub-group D is VI. In a 2nd sub-group D is VII. In a 3rd sub-group D is VIII. In a 4th sub-group D is IX. In a 5th sub-group D is X. In a 6th sub-group D is XI. In a 7th sub-group D is XII. In a 8th sub-group D is XIII. In a 9th sub-group D is XIV. In a 10th sub-group D is XV. In a 11th sub-group D is XVI. In a 12th sub-group D is XVII. In a 13th sub-group D is XVIII.

In a 3rd group the group of formula I has a group of formula IV.

In a 4th group the group of formula I has a group of formula V.

A preferred group of compounds comprises a compound wherein A is a group of formula II wherein R$_1$ and R$_2$ are independently hydrogen, halogen, (C$_{1-4}$)alkyl or alkoxy;

R$_1$ is in position 4 or 5;

R$_3$ is hydrogen or (C$_{1-4}$)alkyl and the corresponding bond is in position 3, 4 or 5;

conveniently Z is S or NR, or

A is a group of formula III wherein R$_4$ is hydrogen, halogen or (C$_{1-4}$)alkoxy, wherein R$_5$ is hydrogen or halogen, R$_6$ is amino, nitro, (C$_{1-4}$)alkylamino, di(C$_{1-4}$)alkylamino, halogen or 1-pyrrolyl, and R$_7$ is hydrogen or halogen, B is CO, C is —O— or —NH— and D is a group of formula VI wherein R$_8$ is hydrogen, (C$_{1-4}$)alkyl or benzyl or D is a group of formula VIII wherein the corresponding bond is in the 3 position.

The following examples illustrate the invention.

EXAMPLE 1

Tablets for oral administration

Tablets containing the constituents as specified below were produced in conventional manner and are used in the indication specified above.

| | |
|---|---|
| Compound E in form of hydrochloride (corresponding to 15 mg free base) | 16.9 mg |
| Hydroxy-propyl-cellulose | 1.2 mg |
| Corn Starch | 12.0 mg |
| Lactose | 92.8 mg |
| Silica | 0.6 mg |
| Magnesium stearate | 1.5 mg |
| Tablet weight | 125.0 mg |

EXAMPLE 2

Capsules for oral administration

Capsules containing the constituents as specified below are produced in conventional manner and are used in the indications specified above.

| | |
|---|---|
| 1-methyl-N(-endo-9-methyl-9-aza-bicyclo-[3,3,1]non-3-yl) carboxylic acid amide in form of the hydrochloride (corresponding to 15 mg base) | 16.9 mg |
| Lactose | 28.7 mg |
| Silica | 1.5 mg |
| Magnesium stearate | 3 mg |

-continued

| | |
|---|---|
| Capsule Content weight of | 300 mg |

EXAMPLE 3

Injection solution for i.v. administration

A composition for injection is made up in conventional manner and is used at a dose of 10 mg a day.

| | A | B | C |
|---|---|---|---|
| Compound E in form of hydrochloride | 1.13[1] | 2.256[2] | 11.282[3] |
| Acetic acid (99 to 100%)* | 1.2 | 0.6 | 0.6 |
| Sodium acetate 3. H$_2$O* | 1.8 | 3.18 | 3.18 |
| Sodium chloride | 8 | 7.5 | 6.5 |
| Water for injection to | 1.0 ml | | |

[1] 1 mg free base,
[2] 2 mg free base,
[3] 10 mg free base pH value 4.3;
Buffer used* 1/30 molar

EXAMPLE 4

Capsules for oral administration 5 mg and 15 mg capsules (A and B respectively) containing the constituents as specified below were produced in conventional manner and are used in the indications specified above 2-4 times a day in the case of A and once a day in the case of B.

| | A mg | B mg |
|---|---|---|
| Compound E in form of hydrochloride | 5.641 | 16.92 |
| Lactose 200 mesh | 84.929 | 79.29 |
| Lactose 100 mesh | 84.43 | 79.29 |
| Corn starch | 120.00 | 120.00 |
| Silica | 1.5 | 1.5 |
| Magnesium stearate | 3.0 | 3.0 |
| | 300 mg | 300 mg |

Capsules containing other weights can be formulated in conventional manner.

The active agents in Examples 1 to 3 may be replaced by the following compounds of formula I wherein:

| Compound No. | A = II, B = —CO— | | | Carboxyl-group in position | C | Conf. | n (VI) D = VIII (pos.) | $R_8$ |
|---|---|---|---|---|---|---|---|---|
| | $R_1$ | $R_2$ | Z | | | | | |
| 1 | H | H | NH | 3 | NH | endo | 3 (VI) | Me |
| 2 | 5-F | H | NMe | 3 | NH | endo | 3 (VI) | Me |
| 3 | H | 2-Cl | NH | 3 | O | endo | 2 (VI) | Me |
| 4 | H | 2-OMe | NH | 3 | O | endo | 2 (VI) | Me |
| 5 | H | 3-J | NH | 4 | O | endo | 2 (VI) | Me |
| 6 | H | H | NH | 4 | O | endo | 2 (VI) | Me |
| 7 | H | H | NH | 4 | O | endo | 3 (VI) | Me |
| 8 | 5-Cl | H | NH | 3 | O | endo | 2 (VI) | Me |
| 9 | 4-OMe | H | NH | 3 | O | endo | 2 (VI) | Me |
| 10 | 5-OMe | H | NH | 3 | O | endo | 2 (VI) | Me |
| 11 | H | H | NMe | 3 | O | endo | 2 (VI) | Me |
| 12 | H | H | NH | 3 | O | exo | 2 (VI) | Me |
| 13 | 5-F | H | NH | 3 | NH | endo | 2 (VI) | Me |
| 14 | H | H | NMe | 3 | NH | endo | 2 (VI) | Me |
| 15 | H | 2-Me | NH | 3 | NH | endo | 2 (VI) | Me |
| 16 | H | H | NH | 3 | NH | exo | 2 (VI) | Me |
| 17 | H | H | NH | 3 | NH | endo | 2 (VI) | Me |
| 18 | 5-Cl | H | NH | 3 | H | endo | 2 (VI) | Me |
| 19 | H | H | NH | 3 | O | endo | 3 (VI) | Bz |
| 20 | H | H | NMe | 3 | O | endo | 3 (VI) | Bz |
| 21 | 5-F | H | NH | 3 | O | endo | 3 (VI) | Bz |
| 22 | H | H | S | 3 | O | endo | 3 (VI) | Me |
| 23 | H | H | S | 3 | NH | endo | 3 (VI) | Me |
| 24 | H | H | O | 3 | NH | endo | 3 (VI) | Me |
| 25 | H | H | O | 3 | O | endo | 3 (VI) | Me |
| 26 | H | H | CH$_2$ | 3 | NH | endo | 3 (VI) | Me |
| 27 | H | H | NH | 3 | NH | exo | 4 (VI) | Me |
| 28 | H | H | NH | 3 | O | exo | 4 (VI) | Me |
| 29 | H | H | NH | 3 | O | endo | 3 (VI) | Me |
| 30 | H | H | NH | 3 | O | endo | 2 (VI) | n-Pr |
| 31 | H | H | NH | 3 | O | exo | 2 (VI) | Bz |
| 32 | H | H | NH | 3 | O | endo | 2 (VI) | Bz |
| 33 | H | H | NH | 3 | O | endo | 2 (VI) | H |
| 34 | 5-F | H | NH | 3 | O | endo | 3 (VI) | H |
| 35 | H | H | NMe | 3 | O | endo | 3 (VI) | H |
| 36 | H | H | NH | 3 | O | endo | 3 (VI) | H |
| 37 | 5-Me | H | NH | 3 | O | endo | 3 (VI) | Me |
| 38 | H | 2-Me | NH | 3 | O | endo | 3 (VI) | Me |
| 39 | 5-F | H | NMe | 3 | O | endo | 3 (VI) | Me |
| 40 | 5-F | H | NH | 3 | O | endo | 3 (VI) | Me |
| 41 | 5-F | H | NMe | 3 | O | endo | 3 (VI) | Bz |
| 42 | H | H | NME | 3 | O | endo | 3 (VI) | Me |
| 43 | 5-Me | H | NH | 3 | NH | endo | 3 (VI) | Me |
| 44 | H | H | NH | 5 | O | endo | 2 (VI) | Me |
| 45 | H | H | NH | 5 | O | endo | 3 (VI) | Me |
| 46 | H | 3-I | NH | 5 | O | endo | 3 (VI) | Me |
| 47 | H | H | NH | 4 | NH | exo | 2 (VI) | Me |
| 48 | H | H | NH | 4 | NH | endo | 2 (VI) | Me |
| 49 | H | H | NH | 5 | H | endo | 2 (VI) | Me |

-continued

| Compound No. | A = II, B = —CO— R₁ | R₂ | Z | Carboxyl-group in position | C | Conf. | n (VI) D = VIII (pos.) | R₈ |
|---|---|---|---|---|---|---|---|---|
| 50 | H | H | NH | 3 | O | — | VIII (3) | — |

| Compound No. | A = III, B = —CO— R₄ | R₅ | R₆ | R₇ | C | Conf. | n(VI) D = VIII (pos) | R₈ |
|---|---|---|---|---|---|---|---|---|
| 51 | OMe | H | NHMe | Cl | O | — | VIII (3) | — |
| 52 | OMe | H | NH₂ | Cl | O | — | 2 (VI) | Bz |
| 53 | OMe | H | NH₂ | Cl | O | exo | 2 (VI) | H |
| 54 | OMe | H | NHMe | Cl | O | endo | 2 (VI) | Me |
| 55 | OMe | H | N(Me)₂ | H | O | exo | 2 (VI) | Bz |
| 56 | OMe | H | NH₂ | Cl | O | endo | 2 (VI) | Me |
| 57 | OMe | H | NH₂ | Cl | O | endo | 2 (VI) | H |
| 58 | OMe | H | NH₂ | H | O | endo | 2 (VI) | H |
| 59 | OMe | H | NH₂ | H | O | exo | 2 (VI) | H |
| 60 | OMe | H | NH₂ | H | O | endo | 2 (VI) | Me |
| 61 | OMe | H | N(Me)₂ | H | O | endo | 2 (VI) | Me |
| 62 | Cl | H | NH₂ | H | O | endo | 2 (VI) | Me |
| 63 | OMe | I | NH₂ | H | O | endo | 2 (VI) | Me |
| 64 | OMe | I | NHMe | H | O | endo | 3 (VI) | Me |
| 65 | OMe | H | NHMe | H | O | endo | 3 (VI) | Me |
| 66 | Cl | H | NO₂ | H | O | endo | 2 (VI) | Me |
| 67 | OMe | H | Br | H | O | endo | 2 (VI) | Me |
| 68 | H | Cl | H | Cl | O | endo | 3 (VI) | Me |
| 69 | OMe | H | 1-Pyrrolyl | Cl | O | endo | 2 (VI) | Me |
| 70 | OMe | H | 1-Pyrrolyl | H | O | endo | 2 (VI) | Me |
| 71 | OMe | H | NHMe | Cl | NH | — | VIII (3) | — |
| 72 | H | Cl | H | Cl | O | — | VIII (3) | — |

| Compound No. | Formula II, B = —CO— R₁ | R₂ | Z | Carboxyl-group in position | C | Conf. | D = group of formula | R₈ |
|---|---|---|---|---|---|---|---|---|
| 73 | H | H | NH | 3 | O | exo | (X) | — |
| 74 | H | H | NH | 3 | O | endo | (XVII) (Z = CH₃)* | CH₃ |
| 75 | H | H | NH | 3 | O | (endo) | (XVI) (r = 3) | CH₃ |
| 76 | H | H | NH | 3 | O | endo | (XI) | CH₃ |
| 77 | H | H | NH | 3 | O | (endo) | (XVI) (r = 2) | CH₃ |
| 78 | H | H | NH | 3 | O | (exo) | (XVI) (r = 3) | CH₃ |
| 79 | H | H | NH | 3 | O | endo | (X) | — |
| 80 | H | H | NH | 3 | O | exo | (XIII) (t = 1) | CH₃ |
| 81 (−) | H | H | NH | 3 | O | endo | (XI) | CH₃ |
| 82 (+) | H | H | NH | 3 | O | endo | (XI) | CH₃ |
| 83 | H | H | NH | 3 | O | endo | (XII) CH₃ | |
| 84 | H | H | NH | 5 | O | endo | (XVII) (Z = OCH₃)* | CH₃ |

( ) = Ring is in chair form
*(1s*, 3r*, 5r*, 6r*)

| Compound No. | Formel III, B = —CO— R₄ | R₅ | R₆ | R₇ | C | Conf. | D = group of formula | R₈ |
|---|---|---|---|---|---|---|---|---|
| 85 | OCH₃ | H | NHCH₃ | Cl | NH | exo | (X) | — |
| 86 | OCH₃ | H | NHCH₃ | Cl | NH | endo | (X) | — |

| Compound No | Formula II B = —CO— R₁ | R₂ | Z | Carboxyl gr. in Position | C | Conf. | Formula XVIII R₈ | R₉ | R₁₀ | R₁₁ | R₁₂ | m | q | o | p |
|---|---|---|---|---|---|---|---|---|---|---|---|---|---|---|---|
| 87 (−) | H | H | —NH— | 3 | —O— | S | CH₃ | H | H | — | — | 2 | 0 | 0 | 1 |
| 88 | H | H | —NH— | 3 | —O— | R | CH₃ | H | H | H | H | 2 | 0 | 0 | 1 |
| 89 | H | H | —NH— | 3 | —O— | RS | CH₃ | H | H | H | H | 1 | 0 | 1 | 0 |
| 90 | H | H | —NH— | 3 | —O— | RS | CH₃ | H | H | H | H | 0 | 1 | 1 | 1 |
| 91 | H | H | —NH— | 3 | —O— | RS | CH₃ | H | H | H | H | 2 | 0 | 1 | 0 |
| 92 | H | H | —NH— | 3 | —O— | RS | CH₃ | H | H | H | H | 1 | 1 | 1 | 0 |
| 93 | H | H | —NH— | 3 | —O— | RS | H | CH₃ | CH₃ | CH₃ | CH₃ | 1 | 1 | 1 | 0 |
| 94 | H | H | —NH— | 3 | —O— | RS | CH₃ | H | H | H | H | 2 | 1 | 1 | 0 |

-continued

| Compound No | Formula II B = —CO— | | | Carboxyl gr. in Position | C | Conf. | Formula XVIII | | | | | | | | |
|---|---|---|---|---|---|---|---|---|---|---|---|---|---|---|---|
| | $R_1$ | $R_2$ | Z | | | | $R_8$ | $R_9$ | $R_{10}$ | $R_{11}$ | $R_{12}$ | m | q | o | p |
| 95 | H | H | —NH— | 3 | —NH— | RS | H | H | H | H | H | 1 | 0 | 1 | 0 |
| 96 | H | H | —NH— | 3 | —NH— | RS | $CH_3$ | H | H | H | H | 1 | 0 | 1 | 0 |

| Compound No. | Formula III, B = —CO— | | | | | | | | | | | | | | |
|---|---|---|---|---|---|---|---|---|---|---|---|---|---|---|---|
| | $R_4$ | $R_5$ | $R_6$ | $R_7$ | C | Conf. | $R_8$ | $R_9$ | $R_{10}$ | $R_{11}$ | $R_{12}$ | m | q | o | p |
| 97 | $OCH_3$ | H | $NH_2$ | Cl | NH | RS | H | H | H | H | H | 1 | 0 | 1 | 0 |
| 98 | $OCH_3$ | H | $NHCH_3$ | Cl | NH | RS | $CH_3$ | H | H | H | H | 0 | 1 | 1 | 1 |

| Compound No. | A = group of Formula | $R_1$ | $R_2$ | X-Y | Z | B | (Position) von B) | C | D = group of form. | (Position von g) | Con. fig. | N | $R_8$ |
|---|---|---|---|---|---|---|---|---|---|---|---|---|---|
| 99 | (II) | H | H | — | NH | CO | (3) | O | (VII) | | anti | 3 | $CH_3$ |
| 100 | (II) | H | H | — | NH | CO | (3) | O | (VII) | | syn | 3 | $CH_3$ |
| 101 | (IV) | H | H | N=CH | — | CO | (3) | O | (VI) | | α | 3 | $CH_3$ |
| 102 | (V) | H | — | — | — | CO | (3) | O | (VI) | | α | 3 | $CH_3$ |
| 103 | (IV) | H | H | CH=CH | — | CO | (2) | O | (VI) | | α | 3 | $CH_3$ |
| 104 | (IV) | H | H | O—$CH_2$ | — | CO | (3) | O | (VI) | | α | 3 | $CH_3$ |
| 105 | (II) | H | H | — | NH | CO | (3) | O | (IX) | | (1S*, 5R*, 6R*,) | — | $CH_3$ |
| 106 | (II) | H | H | — | NH | CO | (3) | NH | (VI) | | anti | 3 | $CH_3$ |
| | | $R_4$ | $R_5$ | $R_6$ | $R_7$ | | | | | | | | |
| 107 | (III) | H | H | $CH_3$ | H | $SO_2$ | — | O | (VIII) | 3 | RS | — | — |
| 108 | (III) | H | H | $CH_3$ | H | $SO_2$ | — | NH | (VIII) | 3 | RS | — | — |
| 109 | (III) | H | O‖C—$NH_2$ | H | H | CO | — | NH | (VIII) | 3 | RS | — | — |
| 110 | (III) | $OCH_3$ | H | H | $SO_2NH_2$ | CO | — | NH | (VIII) | 3 | RS | — | — |
| 111 | (III) | H | H | H | $SO_2NH_2$ | CO | — | NH | (VIII) | 3 | RS | — | — |

What we claim is:

1. A method of treating a serotonin induced gastrointestinal disturbance comprising administering to a subject in need of such treatment a therapeutically effective amount of a compound of formula I:

A-B-C-D     I wherein A is a group of formula II

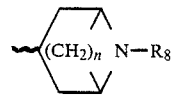

II wherein the free valence is attached to either fused ring,
Z is —$CH_2$—, —$NR_3$—, —O— or —S—;
$R_1$ and $R_2$, independently, are hydrogen, halogen, ($C_{1-4}$)alkyl, ($C_{1-4}$)alkoxy, hydroxy, amino, ($C_{1-4}$)alkylamino, di-($C_{1-4}$)alkylamino, mercapto or ($C_{1-4}$)alkylthio; and
$R_3$ is hydrogen, ($C_{1-4}$)alkyl, ($C_{3-5}$)alkenyl, phenyl or benzyl;
B is —CO— or —$SO_2$—;
C is —O— or —NH—; and
D is a group of formula VI

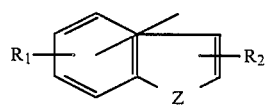

VI wherein n is 2, 3 or 4; and
$R_8$ is hydrogen, ($C_{1-7}$)alkyl, ($C_{3-5}$)alkenyl or benzyl;
or a pharmaceutically acceptable acid addition or quaternary ammonium salt thereof.

2. A method according to claim 1 wherein the compound administered is one wherein $R_1$ and $R_2$, independently, are hydrogen, halogen, ($C_{1-4}$)alkyl or ($C_{1-4}$)alkoxy, $R_1$ is in the 4- or 5-position, $R_3$ is hydrogen or ($C_{1-4}$)alkyl, the free valence is in the 3-, 4- or 5-position, B is —CO—, C is —O— or —NH— and $R_8$ is hydrogen, ($C_{1-4}$)alkyl or benzyl, or a pharmaceutically acceptable acid addition or quaternary ammonium salt thereof.

3. A method according to claim 1 wherein the gastrointestinal disturbance is selected from the group consisting of gastritis, peptic ulcer, biliary dyskinesia, spastic colon, appendicitis, irritable bowel syndrome, Crohn's disease, ulcerative colitis, carcinoid syndrome, secretory diarrhea, bacteria-induced diarrhea, choleric diarrhea, traveller's diarrhea, psychogenic diarrhea, oesophageal motility disturbances, achalasia, hiatus hernia, cardia insufficiency, gastrooesophageal and gastroduodenal reflux, stomach hypotonia, pylorus hyperplasia, paralytic ileus and Hirschsprung's disease.

4. A method according to claim 1 for treating serotonin induced motility and secretion disorders of the gastrointestinal system.

5. A method according to claim 1 for treating diarrhea.

6. A method according to claim 1 for increasing gastric emptying.

7. A method according to claim 1 wherein the compound administered is one wherein Z is —S— or —NR$_3$— wherein R$_3$ is hydrogen or (C$_{1-4}$)alkyl, or a pharmaceutically acceptable acid addition or quaternary ammonium salt thereof.

8. A method according to claim 1 wherein the compound administered is indol-3-yl carboxylic acid endo-8-methyl-8-aza-bicyclo[3.2.1]oct-3-yl ester, or a pharmaceutically acceptable acid addition or quaternary ammonium salt thereof.

9. A method according to claim 7 wherein the compound administered is benzo thiophen-3-yl carboxylic acid endo-8-methyl-9-aza-bicyclo-[3.3.1]non-3-yl ester, or a pharmaceutically acceptable acid addition or quaternary ammonium salt thereof.

10. A method according to claim 7 wherein the compound administered is 5-fluoro-1-methyl-indol-3-yl carboxylic acid endo-9-methyl-9-aza-bicyclo[3.3.1]non-3-yl ester, or a pharmaceutically acceptable acid addition or quaternary ammonium salt thereof.

11. A method according to claim 7 wherein the compound administered is 1-methyl-N(endo-9-methyl-9-aza-bicyclo[3.3.1]non-3-yl)indol-3-yl carboxylic acid amide, or a pharmaceutically acceptable acid addition or quaternary ammonium salt thereof.

12. A method according to claim 8 wherein the compound administered is indol-3-yl carboxylic acid endo-8-methyl-8-aza-bicyclo[3.2.1]oct-3-yl ester hydrochloride.

13. A method according to claim 9 wherein the compound administered is benzo[b]thiophen-3-yl carboxylic acid endo-9-methyl-9-aza-bicyclo[3.3.1]non-3-yl ester hydrochloride.

14. A method according to claim 10 wherein the compound administered is 5-fluoro-1-methyl-indol-3-yl carboxylic acid endo-9-methyl-9-aza-bicyclo[3.3.1]non-3-yl ester hydrogen maleate.

15. A method according to claim 11 wherein the compound administered is 1-methyl-N(endo-9-methyl-9-aza-bicyclo[3.3.1]non-3-yl)indol-3-yl carboxylic acid amide hydrochloride.

16. A method of treating serotonin induced gastroesophageal reflux disorder comprising administering to a subject in need of such treatment a therapeutically effective amount of indol-3-yl carboxylic acid endo-8-methyl-8-aza-bicyclo[3.2.1]oct-3-yl ester, or a pharmaceutically acceptable acid addition or quaternary ammonium salt thereof.

* * * * *